US00PP15365P2

(12) United States Plant Patent
Hooijman

(10) Patent No.: US PP15,365 P2
(45) Date of Patent: Nov. 23, 2004

(54) ***HYPERICUM* PLANT NAMED 'BONAIRE'**

(50) Latin Name: *Hypericum androsaemum*
Varietal Denomination: Bonaire

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/783,354

(22) Filed: Feb. 21, 2004

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of *Hypericum* plant named 'Bonaire', characterized by its upright plant habit; durable dark green-colored leaves; light yellow-colored fruits; and good postproduction longevity.

1 Drawing Sheet

Botanical classification/cultivar designation: *Hypericum androsaemum* cultivar Bonaire.

BACKGROUND OF THE INVENTION

The present Invention relates to a new and distinct cultivar of *Hypericum* plant, botanically known as *Hypericum androsaemum*, commercially used as cut stems with fruits, and hereinafter referred to by the name 'Bonaire'.

The new *Hypericum* is a product of a planned breeding program conducted by the Inventor in El Quinche, Pichincha, Ecuador. The objective of the breeding program was to develop cut *Hypericum* varieties with durable foliage and attractive fruit coloration.

The new cultivar originated from a cross-pollination made by the Inventor in August, 2000 of a proprietary selection of *Hypericum androsaemum* identified as Code 56, not patented, as the female, or seed, parent with a proprietary selection of *Hypericum androsaemum* identified as Code 59, not patented, as the male, or pollen, parent. The cultivar Bonaire was discovered and selected by the Inventor as a flowering plant within the progeny of the stated cross-pollination in a controlled environment in El Quinche, Pichincha, Ecuador.

Asexual reproduction of the new *Hypericum* by terminal cuttings taken at El Quinche, Pichincha, Ecuador since February, 2001, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Bonaire'. These characteristics in combination distinguish 'Bonaire' as a new and distinct cultivar:

1. Upright plant habit.
2. Durable dark green-colored leaves.
3. Light yellow-colored rounded fruits.
4. Good postproduction longevity.

Plants of the new *Hypericum* differ from plants of the female parent selection in the following characteristics:

1. Plants of the new *Hypericum* are shorter than plants of the female parent selection.
2. Plants of the new *Hypericum* have smaller fruits than plants of the female parent selection.
3. Plants of the new *Hypericum* and the female parent selection differ in fruit coloration as plants of the female parent selection have orange-colored fruits.

Plants of the new *Hypericum* differ from plants of the male parent selection primarily in fruit coloration as plants of the male parent selection have dark orange-colored fruits.

Plants of the new *Hypericum* can be compared to plants of the *Hypericum* cultivar Bosapin, disclosed in U.S. Plant Pat. No. 10,993. In side-by-side comparisons conducted in El Quinche, Pichincha, Ecuador, plants of the new *Hypericum* differed from plants of the cultivar Bosapin in the following characteristics:

1. Plants of the new *Hypericum* were shorter than plants of the cultivar Bosapin.
2. Plants of the new *Hypericum* had ovate-shaped leaves whereas plants of the cultivar Bosapin had cordate-shaped leaves.
3. Plants of the new *Hypericum* had smaller fruits than plants of the cultivar Bosapin.
4. Plants of the new *Hypericum* and the cultivar Bosapin differed in fruit coloration as plants of the cultivar Bosapin had red-colored fruits.

BRIEF DESCRIPTION OF THE PHOTOGRAPH

The accompanying colored photograph illustrates the overall appearance of the new *Hypericum*, showing the colors as true as it is reasonably possible to obtain in colored reproductions of this type. Colors in the photograph may differ slightly from the color values cited in the detailed botanical description which accurately describe the colors of the new *Hypericum*. The photograph comprises a side perspective view of a typical flowering stem of Bonaire in fruit.

DETAILED BOTANICAL DESCRIPTION

The new *Hypericum* has not been observed under all possible environmental conditions. The phenotype may vary somewhat with variations in environment such as temperature, daylength and light intensity, without, however, any variance in genotype.

The aforementioned photographs, following observations and measurements describe plants grown in El Quinche, Pichincha, Ecuador, in an outdoor nursery and under commercial production practices. Plants were about six months old when the photograph and description were taken. During the production of the plants, day temperatures ranged from 12 to 30° C. and day temperatures ranged from 5 to 12° C. Plants were pinched about two weeks after planting. In the following description, color references are made to The Royal Horticultural Society Colour Chart, 2001 Edition, except where general terms of ordinary dictionary significance are used.

Botanical classification: *Hypericum androsaemum* cultivar Bonaire.

Parentage:

*Female parent.*—Proprietary selection of *Hypericum androsaemum* identified as Code 56, not patented.

*Male parent.*—Proprietary selection of *Hypericum androsaemum* identified as Code 59, not patented.

Propagation:

*Type.*—Terminal cuttings.

*Time to initiate roots.*—About 7 to 10 days at 22 to 30° C.

*Time to produce a rooted cutting.*—About 28 to 35 days at 22 to 30° C.

*Root description.*—Fibrous, fine; color, N199A.

*Rooting habit.*—Freely branching, moderately dense.

Plant description:

*Plant form.*—Upright and somewhat outwardly spreading perennial woody shrub; erect inverted triangle.

*Growth habit.*—Vigorous. Freely basal branching; dense and bushy growth habit.

*Plant height.*—About 94 cm.

*Plant width (spread).*—About 29 cm.

*Quantity of stems per year.*—About 4.5; production of stems increases with age of plants.

*Lateral branches.*—Length: About 84 cm. Diameter: About 4 mm. Internode length: About 5.7 cm. Strength: Strong. Texture: Smooth, glabrous. Color: 147D overlain with N199D.

*Foliage description.*—Arrangement: Opposite, simple; sessile. Length: About 7.5 cm. Width: About 4.5 cm. Shape: Ovate. Apex: Acute to retuse. Base: Truncate with cordate tendencies. Margin: Entire. Durability: Durable. Texture, upper and lower surfaces: Glabrous, smooth. Venation pattern: Pinnate. Color: Developing leaves, upper surface: 137B. Developing leaves, lower surface: 138B. Fully expanded leaves, upper surface: Close to 139A. Fully expanded leaves, lower surface: 138C. Venation, upper surface: 145A. Venation, lower surface: 143A.

Flower description:

*Flower type and habit.*—Single flowers arranged in terminal compound umbels with about 10 flowers per inflorescence. Flowers fragrant. Flowers not persistent. Flowers face upright.

*Natural flowering season.*—Summer, typically July through early September in The Netherlands; flowering period typically lasts about 60 days.

*Postproduction longevity.*—Cut stems are typically harvested when all flowers have developed fruits. Flowers last about three days on the plant. Postproduction longevity of cut stems with fruits about 14 to 18 days.

*Inflorescence height.*—About 6.5 cm.

*Inflorescence diameter.*—About 6 cm.

*Flower buds.*—Height: About 8 mm. Diameter: About 6 mm. Shape: Globose. Color: 16A.

*Flowers.*—Diameter: About 1.9 cm. Depth: About 1 cm.

*Petals.*—Quantity per flower. Typically five. Length: About 1.1 cm. Width: About 9 mm. Shape: Oval. Apex: Obtuse. Base: Attenuate. Margin: Entire. Aspect: Incurved, concave. Texture, upper and lower surfaces: Smooth, glabrous. Color: Developing and fully expanded petals, upper surface: 13B. Developing and fully expanded petals, lower surface: 13C.

*Sepals.*—Quantity per flower: Typically five. Length: About 1.3 cm. Width: About 1 cm. Shape: Ovate to rounded. Apex: Obtuse. Base: Rounded. Margin: Entire. Aspect: Incurved, concave. Texture, upper and lower surfaces: Smooth, glabrous. Color: Developing and fully developed sepals, upper surface: 141A, towards the base, 142A. Developing and fully developed sepals, lower surface: 138B.

*Peduncles.*—Length: About 4 cm. Diameter: About 2 mm. Orientation: Erect to about 29° from vertical. Strength: Strong. Color: 145A overlain with 176B.

*Pedicels.*—Length: About 1.5 cm. Diameter: About 1.3 mm. Orientation: Erect to about 43° from vertical. Strength: Moderately strong. Color: 145A overlain with 176B.

*Reproductive organs.*—Stamens: Quantity per flower: About 107. Anther shape: Reniform. Anther length: About 0.8 mm. Anther color: 17A. Pollen amount: Moderate. Pollen color: 16A to 21A. Pistils: Quantity per flower: Typically three. Pistil length: About 9 mm. Stigma shape: Rounded. Stigma color: 71A. Style length: About 4 mm. Style color: 150C. Ovary color: 150C.

*Fruits.*—Quantity per flower: One. Type: Capsule. Shape: Broadly ovate. Length: About 1.1 cm. Diameter: About 9 mm. Texture: Smooth, glabrous. Color: 10C, towards the base, 4D.

*Seeds.*—Length: About 0.1 mm. Diameter: About 0.03 mm. Texture: Smooth, glabrous. Color: 200C.

Disease/pest resistance: Plants of the new *Hypericum* have not been observed to be resistant to pathogens and pests common to *Hypericum.*

Temperature tolerance: Plants of the new *Hypericum* have been observed to tolerate temperatures ranging from 0 to 30° C.

It is claimed:

1. A new and distinct cultivar of *Hypericum* plant named 'Bonaire', as illustrated and described.

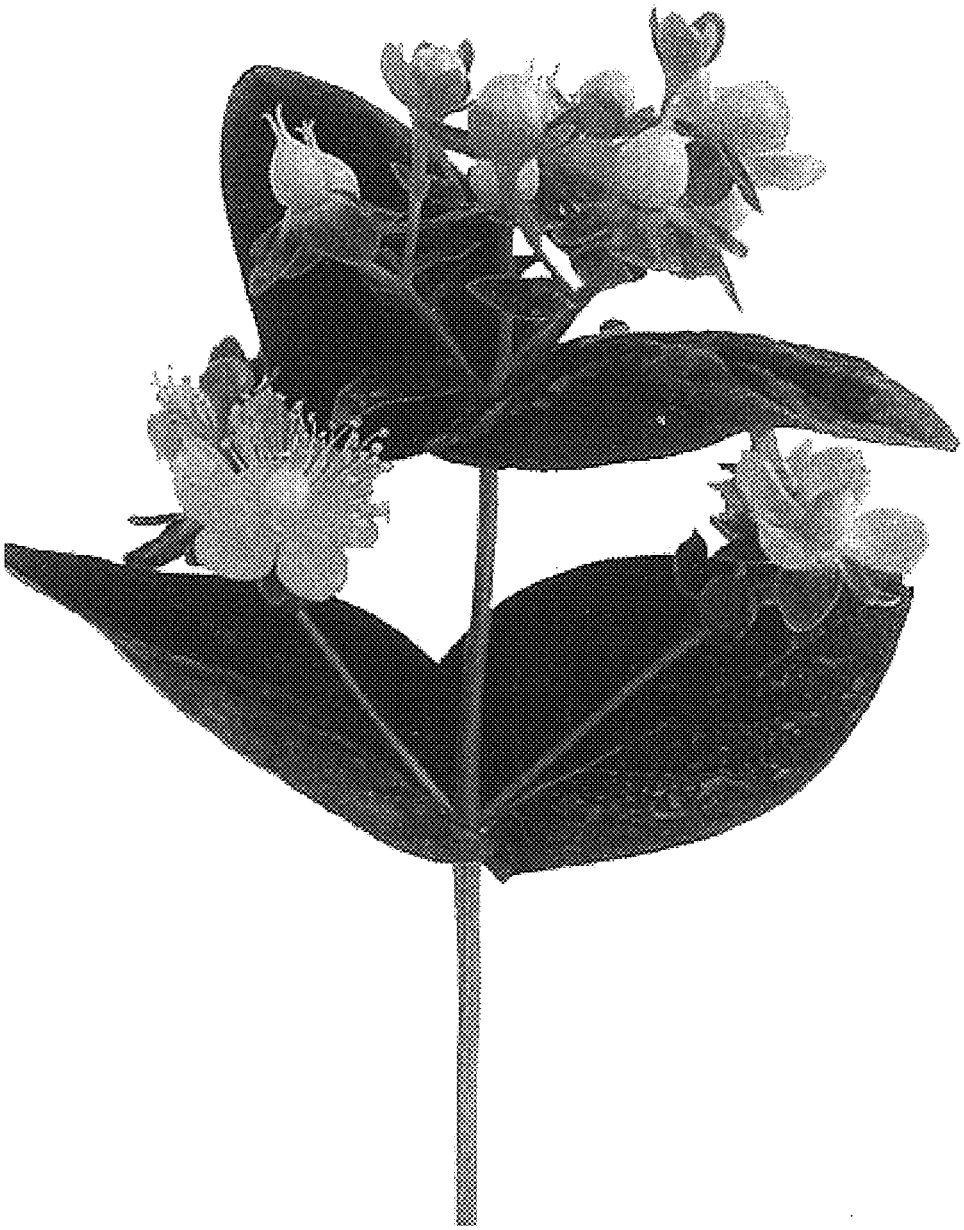

* * * * *